United States Patent [19]

Donald

[11] Patent Number: 4,787,971

[45] Date of Patent: Nov. 29, 1988

[54] MINIATURIZED COLUMN CHROMATOGRAPHY SEPARATION APPARATUS AND METHOD OF ASSAYING BIOMOLECULES EMPLOYING THE SAME

[76] Inventor: Alan Donald, 3330 Second Ave., San Diego, Calif. 92103

[21] Appl. No.: 6,120

[22] Filed: Jan. 23, 1987

[51] Int. Cl.[4] .................................................. B01D 15/08
[52] U.S. Cl. ................................. 210/198.2; 210/657; 422/70; 422/101; 436/178
[58] Field of Search ................... 422/60, 69, 70, 101, 422/102; 436/161, 177, 178; 210/656, 198.2, 657, 282

[56] References Cited

U.S. PATENT DOCUMENTS

| | | | |
|---|---|---|---|
| 3,071,316 | 1/1963 | Piemonte | 422/101 |
| 3,250,395 | 5/1966 | Blume | 422/70 |
| 3,478,886 | 11/1969 | Hornbeck | 210/198.2 |
| 3,519,390 | 7/1970 | Dickey | 422/60 |
| 3,630,683 | 12/1971 | Robb | 422/101 |
| 3,846,077 | 11/1974 | Ohringer | 422/101 |
| 4,024,857 | 5/1977 | Blecher | 422/102 |
| 4,040,791 | 8/1977 | Kuntz | 422/102 |
| 4,138,474 | 2/1979 | Updike | 422/101 |
| 4,142,856 | 3/1979 | Accuff | 436/161 |
| 4,214,993 | 7/1980 | Forsythe | 422/101 |
| 4,234,317 | 11/1980 | Lucas | 422/101 |
| 4,238,196 | 12/1980 | Accuff | 210/198.2 |
| 4,243,534 | 1/1981 | Bulbenko | 210/198.2 |
| 4,247,298 | 1/1981 | Rippie | 422/101 |
| 4,270,921 | 6/1981 | Graas | 210/198.2 |
| 4,277,259 | 7/1981 | Rounbehler | 436/178 |
| 4,301,139 | 11/1981 | Feingers | 210/656 |
| 4,303,615 | 12/1981 | Jarmell | 422/102 |
| 4,311,668 | 1/1982 | Soloman | 422/70 |
| 4,341,635 | 7/1982 | Golias | 210/656 |
| 4,346,613 | 8/1982 | Turner | 422/102 |
| 4,476,016 | 10/1984 | Kiyasu | 422/70 |
| 4,534,939 | 8/1985 | Smith | 422/101 |

Primary Examiner—Ernest G. Therkorn
Attorney, Agent, or Firm—David G. Rosenbaum; Harry M. Weiss

[57] ABSTRACT

The present invention is directed to providing a column chromatography apparatus and assay method employing the same which is readily adaptable for rapid laboratory separation of chemicals, in particular, organic, inorganic and biochemicals and biomolecules from an eluent fluid, such as a body fluid. In particular, it has been determined that a miniaturized column chromatography apparatus having a multi-stage separatory tube, an associated eluent tube, an adapter and a vented-cap and a non-vented cap is particularly well suited to the rapid assays yielding accurate results which are required in the analytical laboratory or clinical setting.

24 Claims, 2 Drawing Sheets

MINIATURIZED COLUMN CHROMATOGRAPHY SEPARATION APPARATUS AND METHOD OF ASSAYING BIOMOLECULES EMPLOYING THE SAME

BACKGROUND OF THE INVENTION

This invention relates generally to an apparatus for separation of liquid compounds by column chromatography. More particularly, the present invention relates to a miniaturized chromatography column for the rapid separation of organic chemicals, inorganic chemicals, biochemicals and biomolecules by liquid phase chromatography.

It has been found that traditional column chromatography apparatus are not easily adapted for the rapid separation of biomolecules in a laboratory setting. Where there is a need for separation of compounds from a body fluid, such as blood or urine, a laboratory technician must set up individual columns for each type of separation to be done. The process of setting up a column consists of selecting the appropriate stationary phase medium specific to the biochemical or body fluids to be separated and packing the column with the appropriate stationary phase medium. After setting up the conventional column chromatography apparatus, the technician is then able to introduce the eluent into the column and collect the eluate, then recover the separated biochemical from the stationary phase media by appropriate washings.

Conventional column chromatography apparatus provide inherently slow separations due to the length of the column or the quantity of biochemical to be separated. Numerous methods of accelerating the separations have been developed, such as use of a pump to forcedly move the eluent through the column or plungers to maintain a pressure gradient on the eluent. None of the conventional column chromatography apparatus, however, are well adapted for diagnostic, analytical or other laboratory procedures where rapid separations of biochemicals or biomolecules from body fluids are required.

Conventional column chromatography apparatus consist of glass buret-like tubes which are packed with a separatory medium. The size and length of these conventional apparatus make them unsuitable for use in rapid separations with high recovery yields. Further, conventional chromatography apparatus require the repetitive transfer of the eluate or subsequent washes to a multitude of vessels. The necessity for the use of many vessels to collect the eluate and wash increases the likelihood of contamination in the separated biochemical and, therefore, increases the likelihood of erroneous analytical or diagnostic results. Finally, conventional chromatography apparatus are typically capable of single-stage separations whereby only one type of eluent or one type of separation media may be employed. It has been found desirable to provide a miniaturized column chromatography apparatus which will meet the foregoing deficiencies commonly found with conventional column chromatography apparatus. The present invention, therefore, is directed to providing a column chromatography apparatus which is readily adaptable for rapid laboratory separation of biochemicals and biomolecules from an eluent fluid, such as a body fluid. In particular, it has been determined that a miniaturized column chromatography apparatus having a multi-stage separatory tube, an associated eluent tube, a vented-cap and a non-vented cap wherein the entire apparatus is sized to be usable with a common laboratory centrifuge or, if necessary, an ultracentrifuge and is adapted to fit conventional test tubes, holder racks, mini-vials, syringes and other laboratory equipment. By providing a column chromatography apparatus configured in this manner, a laboratory technician is able to rapidly separate biomolecules from the eluent fluid, recover and quantify the desired biochemical.

SUMMARY OF THE INVENTION

Accordingly it is an object of the present invention to provide a column chromatography apparatus for the rapid liquid phase separation of chemicals, and in particular, biochemicals and biomolecules.

It is another object of the present invention to provide a column chromatography apparatus for ion exchange, molecular weight, adsorption/partition, hydroxylapatite, particular removal, semi-affinity and affinity chromatography separations.

It is yet another object of the present invention to provide a column chromatography apparatus for multistage separations in a unitary apparatus.

It is still another object of the present invention to provide a column chromatography apparatus adapted for use with a common laboratory centrifuge or ultracentrifuge.

It is still yet another object of the present invention to provide a column chromatography apparatus adapted for use with a syringe so that syringe-injected air may be utilized to create a fluid flow force.

It is a further object of the present invention to provide a column chromatography apparatus having a vented and non-vented cap for sealing the column during separation or sealing the eluate after collection.

It is another further object of the present invention to provide a column chromatography apparatus having an eluate collection portion adapted for use with laboratory analytical devices.

The aforementioned objects are accomplished, according to the present invention, by providing a column chromatography apparatus having a multi-stage separation column portion, an eluate collection portion, an adapter portion, a vented cap portion and a non-vented cap portion.

The foregoing objects, features and advantages of this invention will be apparent from the following, more particular, description of the preferred embodiments of this invention, as illustrated in the accompanying drawings, wherein like features are identified by like numerals.

DESCRIPTION OF THE PREFERRED EMBODIMENTS

Figure 1:
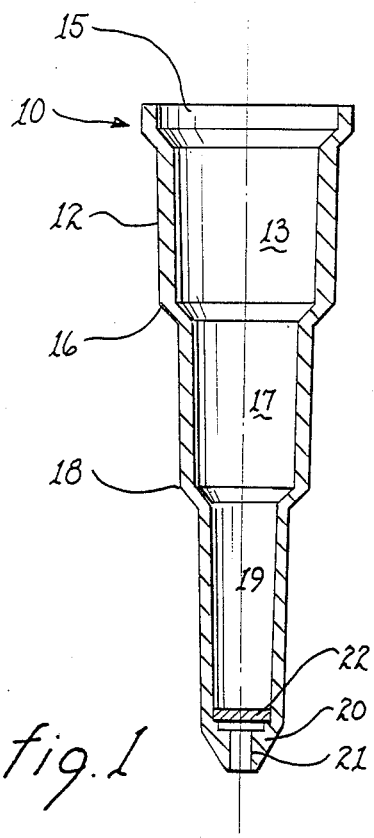
FIG. 1 is a side elevational cross-sectional view of a column chromatography apparatus according to the present invention illustrating the multi-stage separation column portion.
Figure 1A:
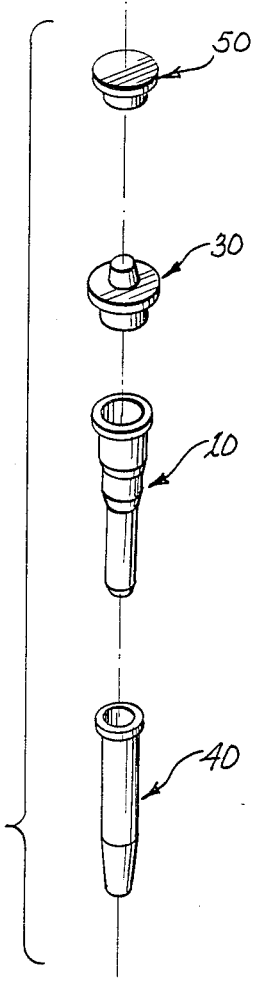
FIG. 1a is a perspective exploded view of the miniaturized column chromatography apparatus according to the present invention.

Turning to the accompanying Figures, in which like features are identified by like numerals, the preferred embodiment of a column chromatography apparatus 10 is illustrated. As illustrated by FIG. 1, column chromatography apparatus 10 is ideally suited for laboratory and clinical use for rapid separations of organic, inorganic and biochemicals, as well as biomolecules by liquid phase chromatography. Liquid phase chromatography entails the introduction of a fluid, e.g., blood plasma or urine, into a column packed with a suitable separatory medium, the selection of which depends upon the chemical sought to be separated. After allowing the eluent to course through the length of the column, the eluate is collected in a suitable receptacle. Typically, the scientist, technician or clinician will select a separatory medium for separating the desired biochemical or biomolecule from the eluent. To collect the desired biochemical or biomolecule, the column is washed with a suitable wash, typically an aqueous acid or base, and this wash is collected and assayed. Repeated washings may recover additional quantities of the desired biochemical or biomolecule.

Column chromatography apparatus 10 consists of a generally tubular column member 12 which has an eluant inlet opening 15 and an elutate outlet opening 21. According to the present invention eluent inlet opening 15 has a diameter which is relatively greater than the diameter of eluate outlet opening 21. Since many biochemical assays must be performed at cold temperatures, the intermediates or products of these assays are frequently stored at extremely cold temperatures (as low as $-100°$ C.), to avoid denaturation of proteinaceous biomolecules, the material of choice for tubular column member 12 must be thermally stable across a wide temperature range. In addition, the material must be stable in the presence of a diversity of chemicals, particularly aqueous acids or bases and be capable of withstanding the forces of sterilization by gamma and beta irradiation and gaseous ethylene oxide. It is preferable, therefore, that tubular column member 12 be made of a material, such as an ethylene-polypropylene plastic, which is sufficiently chemically and thermally inert to the above. It is further preferable to employ a plastic which is inexpensive and, thereby, disposable. According to the preferred embodiment of the present invention, tubular column member 12 is constructed of a unitary piece of milled and bored, or injection molded plastic such as that marketed by Eastman Chemical Products under the trademark TEMITE. It has been found that TENITE No. 7583-353A is particularly well suited for use with the present invention.

Tubular column member 12 tapers along its lengthwise axis, gradually tapering from eluent input opening 15 to eluate outlet opening 21. A filter 22 is horizontally disposed adjacent to and subtending the eluent outlet 21. Filter 22 preferably consists of a microporous polymeric plastic filter. It has been found that filters made of polyethylene, polypropylene, polyether-polyurethane, polyester-polyurethane, polyolefin, polyvinylidene flouride, ethylene-vinyl acetate, styrene-acrylonitrile or polytetrafluoroethylene are particularly well-suited to use in the present invention. Examples of such polymeric plastics include those marketed under the trademark INTERFLO by Chromex Corporation of New York, VYON, PERMAIAR, PORELLE by Pore Technology, Ltd. of Somerville, Mass. or POREX by Porex Technologies, Corp. of Fairburn, Ga. Each of these polymeric plastics are sufficiently chemically and thermally inert to render them particularly well suited for use in the inventive miniaturized column chromatography apparatus.

It is preferable, according to the preferred embodiment of the present invention, to provide a tubular column member 12 having a plurality of chambers 13, 17 and 19 defined by successive constrictions 16 and 18 in the diameter of tubular column member 12. Such a multi-chambered tubular column member, the technician may be packed with a single separatory medium or packed as a multi-stage separatory column. Where a single separation is required, the entire column length, or any portion thereof, may be packed with a suitable separatory medium. Where multiple separations are required, however, a single column may be differentially packed with different separatory media to achieve multiple separations. It will be recognized by those skilled in the art, that the feature of a plurality of increasingly larger diameter chambers increases the stack height of, and therefore the efficiency of, the separatory material or materials. As an example, 100 mg of a separatory medium is more efficient in a $\frac{1}{4}$-inch diameter column than in a one-inch column. Increased stack height of the separatory medium can provide a proportional increase in surface area for the eluent to contact. Accordingly, it is advantageous to provide, as in the present invention, a column which optimizes the efficiency of the separatory medium by increasing its stack height through a plurality of increasingly larger diameter chambers.

By providing a tubular column member 12 having a plurality of chambers 13, 17 and 19, it is possible to separate chambers 13, 17 and 19 by disposing polymeric filters 22 therebetween at constrictions 16 and 18 respectively or at any other point along the taper of each chamber. Separation of the column into a plurality of contiguous, but differential chambers permits the successive separation of different biochemical or biomolecules with different separatory media.

It will be understood, by those skilled in the art, that any suitable separatory media and associated separatory method may be employed. In particular, the present miniaturized column chromatography apparatus is particularly well suited to rapid ion exchange, molecular weight, adsorption/partition, hydroxylapatite, particulate removal, semi-affinity and affinity chromatography separations. Accordingly, suitable separatory media include, but are not limited to, ion exchange resin, ion exchange cellulose, ion exchange gel, sephadex, silica gel, alumina, hydroxylapatite gel, phenylborate cellulose and affinity gel. Thus, it can be readily acknowledged by those skilled in the art, that the present invention has a broad utility across the wide range of analytical and clinical chromatographic separations.

Figure 2:
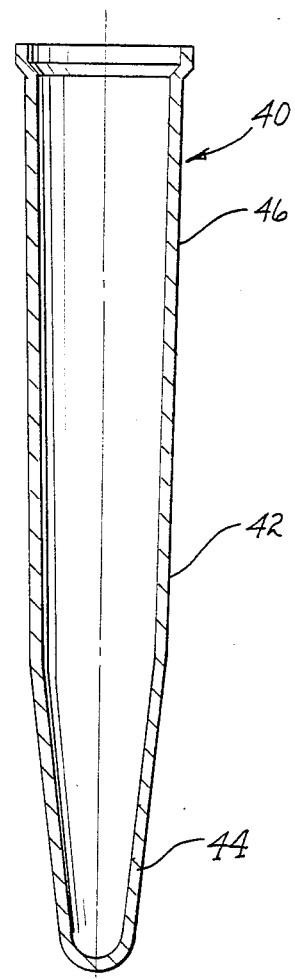
FIG. 2 is a side elevational cross-sectional view of a column chromatography apparatus according to the present invention illustrating the eluate collection portion thereof.

To increase the broad utility of the present invention, it has been found desirable to provide an entire miniaturized column chromatography apparatus consisting of a tubular column member 12, a receptacle container 40, a cap member 50 and an adapter 30. As illustrated by FIG. 2, receptacle container 40 consists of an elongated tapering tubular member 42 having a tapering frusto-conical shaped lower portion 44. An upper rim portion 46 of receptacle container 40 has an inner diameter which is configured to securely couple the outside diameter of a surface of tubular column member 12. By providing corresponding inner and outer diameters of tubular column member 12 and receptacle container respectively, the technician, scientist or clinician will be able to fit the miniaturized column chromatography apparatus 10 in a standard test tube rack and standard laboratory centrifuges and ultracentrifuges without danger of adversely affecting the column or separation.

Figure 3:
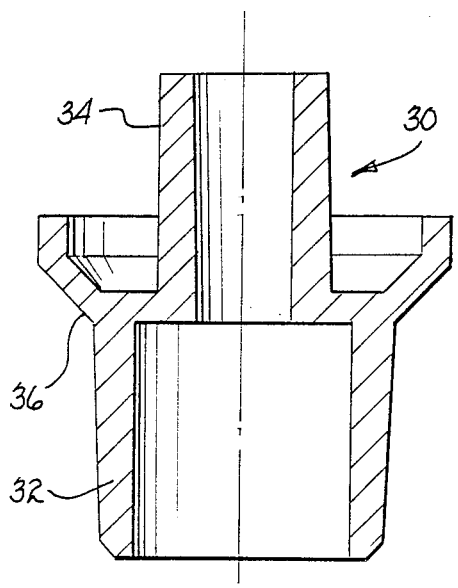
FIG. 3 is a side elevational cross-sectional view of a column chromatography apparatus according to the present invention illustrating the adapter portion thereof.
Figure 4:
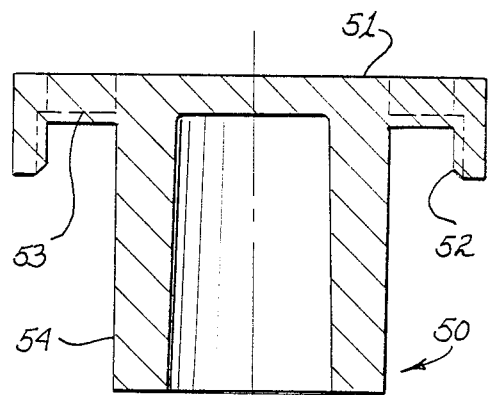
FIG. 4 is a side elevational cross-sectional view of a cap portion of a column chromatography apparatus according to the present invention.
Figure 5:
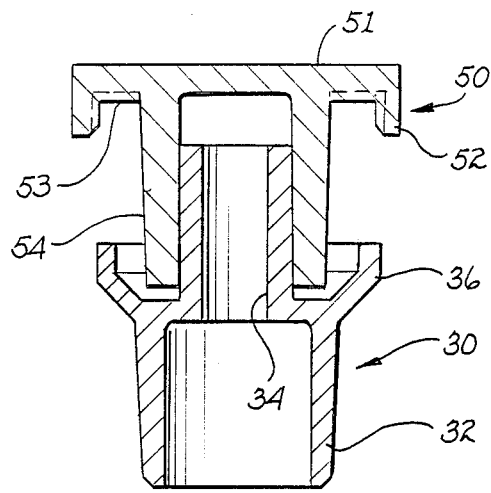
FIG. 5 is a side elevational cross-sectional view of a cap portion communicating with an adapter portion of a column chromatography apparatus according to the present invention.
Figure 6:
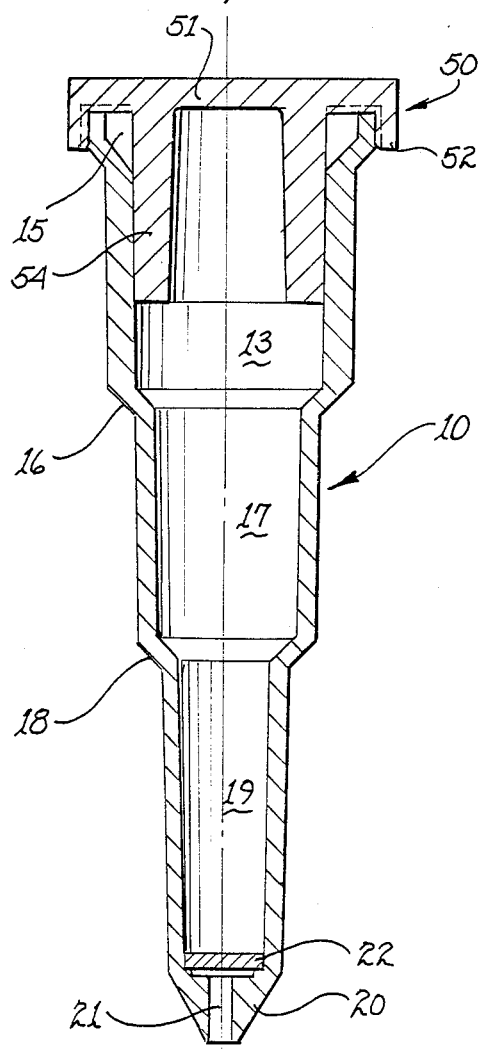
FIG. 6 is a side elevational cross-sectional view of a cap portion communicating with a multi-stage separation column portion of the miniaturized column chromatography apparatus according to the present invention.
Figure 7:
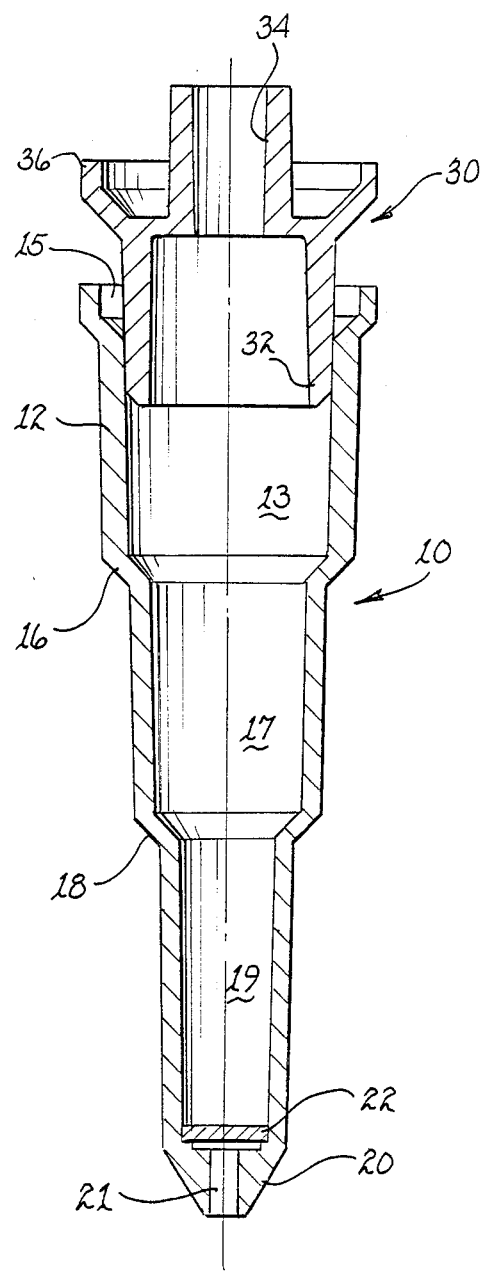
FIG. 7 is a side elevational view of an adapter portion communicating with a multi-stage separation column portion of the inventive miniaturized column chromatography apparatus.

With reference to FIGS. 3, 4 and 5, there is shown the adapter and cap of the present invention. Cap 50 and adapter 30 are configured for multiple uses as either vented or non-vented coverings for tubular column member 12 along, tubular column member in combination with receptacle container 40 in FIG. 2 or receptacle container 40 in FIG. 2 alone. Ideally, cap 50 consists of a generally cylindrical hollow lower stalk portion 54 and a generally planar upper cap portion 51 integrally extensible from upper cap portion 51 and disposed thereupon. Upper cap portion 51 further has a lower ring portion 52 depending from the outer periphery of upper cap portion 51. It is especially desirable, according to the contemplated preferred embodiment of the present invention, to configure hollow lower stalk portion 54 so that its outside diameter will engage within the inside diameter of an upper rim portion 14 of generally tubular column member 12. Hollow lower stalk portion 54 is configured so that its outer diameter directly corresponds to the inner diameter of the upper rim portion 46 of receptacle container 40 in FIG. 2, thereby creating a non-vented closure for receptacle container 40. Further, as depicted in FIG. 6, cap 50 is ideally configured so that the inside diameter of lower ring portion 52 corresponds to the outside diameter of the upper rim portion 14 of tubular column member 12, thereby providing a vented closure for tubular column member 12.

It is necessary, however, that cap 50 provide some means for venting air into the column to counteract the negative pressure created by the fluid flow through the column. Accordingly, it has been found preferable to provide venting means 53 on cap 50. The best mode for providing venting means 53, as contemplated according to the present invention, is to provide a plurality of venting protrusions 53 extending radially across the inner surface of upper cap portion 51 and lower ring portion 52. The provision of venting protrusions 52 permits the free flow of eluent fluid through the column without the creation of negative pressure due to its flow through the column. Moreover, venting protrusions 52 permit a vented seal to be made between cap portion 50 and tubular column member 12 while minimizing the possibility of contamination during handling.

Adapter 30 is provided to allow usage of tubular column member 12 with syringes for injecting air into tubular column member 12. Adapter 30 consists of generally cylindrical hollow upper portion 34, a generally cylindrical hollow lower portion 32 depending therefrom and a radial flange 36 extending outwardly at the junction of upper portion 34 and lower portion 32. As shown in FIG. 5, hollow upper portion 34 is configured to have an outside diameter which corresponds to the inner diameter of the lower stalk portion 54 of cap 50. It is also desirable, according to the preferred embodiment of the present invention to configure hollow upper portion 34 of adapter 30 so that its inner diameter corresponds to the universal luer taper standard for syringes and other medical luers as set forth by the American National Standards Institute in "Glass and Metal Luer Tapers for Medical Applications." An adapter 30 having a standardized hollow upper portion 34 is capable of being used with most standard syringe luers. Hollow lower portion 32 is configured to have an outside diameter which corresponds to the inside diameter of the upper portion 14 of tubular column member 12.

It has been found that by employing the present miniaturized column chromatography apparatus in conventional biochemical assays, an unexpected improvement in assay accuracy has been demonstrated. For example, a present method of assaying catecholamines in plasma, urine and cerebrospinal fluid entails introduction of the eluent into a test tube to which finely powdered alumina is added. The tube is gently agitated for several minutes and centrifuged to pelletize the alumina. Upon removal from the centrifuge, the supernatant is carefully removed by hand-pipetting and discarded. The alumina is resuspended in the tube in an acid wash, allowed to react for several minutes, and recentrifuged to pelletize the alumina. The supernatant is then removed by hand pipetting and introduced into a second tube for further steps in the procedure to quantify catecholamines. Several washes with acid and their requisite centrifugations and careful removal of the supernatant may be necessary to fully recover the catecholamine fraction. It will be recognized by those skilled in the art, that the repetition of each hand-performed operation increases the likelihood of contamination and human error.

In contradistinction to present assay methods, the present invention further provides a method of assaying biomolecules which is particularly well suited for rapid analytical or clinical column chromatography separations. In particular, it has been found that about a 12–15% improvement in recovery has been achieved by employing the present miniaturized column chromatography apparatus in the present inventive method. As examples of the present method, but not to be understood as limiting the present invention, catecholamine assays were run as follows:

EXAMPLE I

Aliquots of 10 $\mu$l of a concentrated tritiated norepinephrine ($^3$H-NE) solution, suspended in a Tris buffer with 0.1 mM of dithiothreitol (DTT, 0.154 mg/ml) as an antioxidant, were added to each of three miniaturized column chromatography apparatuses (A, B and C) according to the present invention. Each of the columns was centrifuged and the eluates collected. The columns were then washed four times each with 4 ml of a deionized water/DTT solution at 4° C. Eluates were collected and radioactivity was counted in a scintillation counter. Subsequently, column A was washed three times, each with 200 ul of 0.1N HCl; the eluates were similarly collected and counted. In a like manner, columns B and C were washed three times each with 200 ul of 0.5N HCl; the eluates were collected and counted. The percent recoveries of norepinephrine are summarized by the following table:

TABLE A

| Wash | Column A | Column B | Column C |
|---|---|---|---|
| Water: | 2.0% | 2.1% | 4.9% |
| Acid | | | |
| 0.1 N HCl | 78.5% | — | — |
| 0.5 N HCl | — | 75% | 81.0% |

EXAMPLE II

The same procedures were followed as in Example I, above, except 10 ul of the $^3$H-NE diluted solution was added to 0.1 mM DTT solution, 1000 pg/nl non-radioactive dopamine, epinephrine and norepinephrine (DEN) was added. The resulting solution was then introduced into three columns packed as follows:
Column A: 50 mg alumina
Column B: 100 mg alumina
Column C: 200 mg alumina
After water washes followed by three washes each with 200 ul 0.1N HCl and one wash of 200 ul 0.5N HCl the following recoveries were obtained:

TABLE B

| Wash | Column A | Column B | Column C |
|---|---|---|---|
| Water: | 5.2% | 2.6% | 0.8% |
| Acid: | 48.33% | 64.35% | 63.45% |

Thus, it will be readily noted, by those skilled in the art, that excellent recoveries are possible with the assay according to the present invention. In particular, as indicated by the aforementioned Examples, a catecholamine assay following the present invention is best carried out utilizing three washes of 0.5N HCl and either a 100 mg or 200 mg alumina packed column.

While the invention has been particularly shown and described in reference to the preferred embodiments thereof, it will be understood by those skilled in the art that changes in form and details may be made without departing from the spirit and scope of the invention.

I claim:

1. A miniaturized column chromatography apparatus, comprising:
   a generally tubular column member having a plurality of chambers, each of said plurality of chambers being disposed in fluid flow communication with another of said plurality of chambers, said tubular column member further having an eluent inlet and eluate outlet, said inlet having a relatively larger diameter than and in fluid flow communication with said eluate outlet, said eluate outlet further having a generally frusto-conical shape;
   a planar disc-shaped porous filter horizontally disposed within said generally tubular column member and subtending said eluate outlet;
   chromatographic separatory medium packed within said generally tubular column member, said chromatographic separatory medium being selected dependent upon the materials to be separated;
   vented capping means for closing said eluate inlet disposed within eluate inlet opening and comprising a cap and a cap adapter, wherein said cap further comprises a generally cylindrical hollow lower stalk portion and a generally planar upper cap portion having a lower ring portion depending therefrom, wherein said lower ring portion has an inside diameter corresponding to an outside diameter of an upper rim portion of said generally tubular column member; and wherein said cap adapter further comprises a generally cylindrical hollow upper portion, a generally cylindrical hollow lower portion depending therefrom and a radial flange extending outwardly from an upper surface of said generally cylindrical lower portion, said upper portion having outside diameter corresponding to an inner diameter of said generally cylindrical hollow lower stalk portion of said cap and said lower portion having an outside diameter corresponding to an inside diameter of an upper portion of said generally tubular column member; and
   an eluate receiving member having a rounded bottom portion for forming a pellet therein; said eluate receiving member being disposed in fluid communication with said generally tubular column member.

2. The miniaturized column chromatography apparatus according to claim 1, wherein each of said plurality of chambers further comprising an outlet and an inlet opening thereto, wherein each of said outlet openings has a relatively smaller diameter than each of said associated inlet openings.

3. The miniaturized column chromatography apparatus according to claim 2, wherein said generally tubular column member further a unitary column member constructed of a chemically and thermally inert plastic material.

4. The miniaturized column chromatography apparatus according to claim 2, wherein said generally tubular column member further comprises a unitary column member constructed of an ethylene and propylene plastic.

5. The miniaturized column chromatography apparatus according to claim 2, wherein each of said outlet openings further comprises a porous filter subtending said outlet opening.

6. The miniaturized column chromatography apparatus according to claim 5, wherein each of said plurality of chambers further comprises different chromatographic separatory media packed therein, each of said different chromatographic separatory media being selected dependent upon the materials to be separated.

7. The miniaturized column chromatography apparatus according to claim 6, wherein said chromatographic separatory medium is selected from the group consisting of ion exchange resin, ion exchange cellulose, ion exchange gel, sephadex, silica gel, alumina, hydroxyapatite gel, phenylborate cellulose and affinity gel.

8. The miniaturized column chromatography apparatus according to claim 2, wherein said chromatographic separatory medium is selected from the group consisting of ion exchange resin, ion exchange cellulose, ion exchange gel, sephadex, silica gel, alumina, hydroxyapatite gel, phenylborate cellulose and affinity gel.

9. The miniaturized column chromatography apparatus according to claim 1, wherein said generally tubular column member further comprises a unitary column member constructed of a chemically and thermally inert plastic material.

10. The miniaturized column chromatography apparatus according to claim 1, wherein said generally tubular column member further comprises a unitary column member constructed of an ethylene and propylene plastic.

11. The miniaturized column chromatography apparatus according to claim 1, wherein said porous filter further comprises a polymeric plastic material.

12. The miniaturized column chromatography apparatus according to claim 1, wherein said porous filter further comprises a polymeric plastic material selected from the group consisting of polyethylene, polypropylene, polyether-polyurethane, polyester-polyurethane, polyolefin, polyvinylidene flouride, ethylene-vinyl acetate, styrene-acrylonitrile and polytetrafluoroethylene.

13. The miniaturized column chromatography apparatus according to claim 1, wherein said generally tubular column member further comprises a plurality of said porous filters horizontally disposed therein forming a plurality of chambers therebetween.

14. The miniaturized column chromatography apparatus according to claim 13, wherein each of said plurality of chambers further comprises different chromatographic separatory media packed therein, each of said different chromatographic separatory media being selected dependent upon the materials to be separated.

15. The miniaturized column chromatography apparatus according to claim 1, wherein each of said chambers further comprises a porous filter horizontally disposed within said chamber and subtending an outlet opening thereof.

16. The miniaturized column chromatography apparatus according to claim 15, wherein each of said plurality of chambers further comprises different chromatographic separatory media packed therein, each of said different chromatographic separatory media being selected dependent upon the materials to be separated.

17. The miniaturized column chromatography apparatus according to claim 1, wherein said chromatographic separatory medium is selected from the group consisting of ion exchange resin, ion exchange cellulose, ion exchange gel, sephadex, silica gel, alumina, hydroxyapatite gel, phenylborate cellulose and affinity gel.

18. The miniaturized column chromatography apparatus according to claim 1, wherein said multi-stage column member further comprises a plurality of said porous polymeric filters subtending an outlet opening of at least one of said chambers of said multi-stage column member.

19. The miniaturized column chromatography apparatus according to claim 18, wherein each of said plurality of chambers having an outlet opening subtended by said porous polymeric filters further comprises different chromatographic separatory media packed therein, each of said different chromatographic separatory media being selected dependent upon the materials to be separated.

20. A miniaturized column chromatography apparatus, comprising, in combination:
   a multi-stage column member having an eluate inlet and eluent outlet opening and a plurality of chambers in fluid flow communication disposed therebetween, each of said chambers having an inlet and outlet opening, each of said inlet openings further having a relatively larger diameter than a communicating outlet opening, said eluate outlet further having a generally frustro-conical shape and a central bore passing therethrough;
   at least one of a plurality of porous polymeric disc-shaped filters horizontally disposed within said multi-stage column member and subtending said eluate outlet and at least one of said outlet openings of said plurality of chambers;
   at least one of a plurality of chromatographic separatory media packed within said generally tubular generally tubular column member, said chromatographic separatory media being selected dependent upon the materials to be separated wherein a different and distinct one of said at least one of a plurality of chromatographic separatory media is packed in each of said plurality of chambers of said multi-stage column member for separating different and distinct materials from a solution;
   a cap member having a generally cylindrical hollow lower stalk portion and a generally planar upper cap portion having a lower ring portion depending therefrom, wherein said lower ring portion has an inside diameter corresponding to an outside diameter of an upper rim portion of said generally tubular column member;
   a cap adapter having a generally cylindrical hollow upper portion, a generally cylindrical hollow lower portion depending therefrom and a radial flange extending outwardly from an upper surface of said generally cylindrical lower portion, said upper portion having outside diameter corresponding to an inner diameter of said generally cylindrical hollow lower stalk portion of said cap and said lower portion having an outside diameter corresponding to an inside diameter of an upper portion of said generally tubular column member; and
   an eluate receiving member disposed in fluid communication with said generally tubular column member.

21. The miniaturized column chromatography apparatus according to claim 20, wherein said generally tubular column member further comprises a unitary column member constructed of a chemically and thermally inert plastic material.

22. The miniaturized column chromatography apparatus according to claim 20, wherein said porous polymeric filter further comprises a plastic material selected from the group consisting of polyethylene, polypropylene, polyether-polyurethane, polyester-polyurethane, polyolefin, polyvinylidene fluoride, ethylene-vinyl acetate, styrene-acrylonitrile and polytetrafluoroethylene.

23. The miniaturized column chromatography apparatus according to claim 20, wherein said chromatographic separatory medium is selected from the group consisting of ion exchange resin, ion exchange cellulose, ion exchange gel, sephadex, silica gel, alumina, hydroxyapatite gel, phenylborate cellulose and affinity gel.

24. The miniaturized column chromatography apparatus according to claim 20, wherein said cap portion of said capping means further comprises venting means disposed on said cap portion for alleviating negative pressure within said generally tubular column member during a separation run.

* * * * *